(12) United States Patent
Gao et al.

(10) Patent No.: US 12,089,618 B2
(45) Date of Patent: Sep. 17, 2024

(54) RAPID FERMENTATION METHOD FOR SHRIMP PASTE BASED ON COMBINED STRAIN FORTIFICATION

(71) Applicant: JIANGSU UNIVERSITY, Zhenjiang (CN)

(72) Inventors: Ruichang Gao, Zhenjiang (CN); Ying Li, Zhenjiang (CN); Huijie Liu, Zhenjiang (CN); Li Yuan, Zhenjiang (CN); Tong Shi, Zhenjiang (CN)

(73) Assignee: JIANGSU UNIVERSITY, Zhenjiang (CN)

( * ) Notice: Subject to any disclaimer, the term of this patent is extended or adjusted under 35 U.S.C. 154(b) by 0 days.

(21) Appl. No.: 18/572,802

(22) PCT Filed: Dec. 28, 2022

(86) PCT No.: PCT/CN2022/142877
§ 371 (c)(1),
(2) Date: Dec. 21, 2023

(87) PCT Pub. No.: WO2023/226430
PCT Pub. Date: Nov. 30, 2023

(65) Prior Publication Data
US 2024/0260625 A1    Aug. 8, 2024

(30) Foreign Application Priority Data

May 25, 2022  (CN) .......................... 202210571850.1

(51) Int. Cl.
| | | |
|---|---|---|
| *A23L 17/00* | (2016.01) | |
| *A23L 17/40* | (2016.01) | |
| *C12N 1/14* | (2006.01) | |
| *C12N 1/20* | (2006.01) | |
| *C12R 1/46* | (2006.01) | |
| *C12R 1/645* | (2006.01) | |

(52) U.S. Cl.
CPC .............. *A23L 17/65* (2016.08); *A23L 17/40* (2016.08); *C12N 1/145* (2021.05); *C12N 1/205* (2021.05); *C12R 2001/46* (2021.05); *C12R 2001/645* (2021.05)

(58) Field of Classification Search
CPC .......... A23L 17/40; A23L 17/65; A23L 17/70; A23L 27/24; C12N 1/02; C12N 1/20; C12N 1/14; C12N 1/205; C12N 1/145; A23V 2400/225; C12R 2001/46; C12R 2001/645
See application file for complete search history.

(56) References Cited

FOREIGN PATENT DOCUMENTS

| | | | |
|---|---|---|---|
| CN | 106635912 A | 5/2017 | |
| CN | 106820082 A | 6/2017 | |
| CN | 112753994 A | 5/2021 | |
| CN | 115024482 A | 9/2022 | |
| JP | 2008237141 A | 10/2008 | |

OTHER PUBLICATIONS

Yang H., CN-111000204-A, English Machine Translation, Apr. 14, 2020, pp. 1-4 (Year: 2020).*
Ying Li, Study on Formation Mechanism of Key Volatile Flavor Compounds in Traditional Shrimp Paste and Rapid Fermentation by Strengthening Strains, Jiangsu University Professional degree master's Thesis, 2022, pp. 1-112.
GB5009.228-2016, Determination of votalite basic nitrogen in food, National food safety standards, 2016, pp. 1-8, National Health and Family Planning Commission of the People's Republic of China.
GB5009.235-2016, Determination of amino acid nitrogen in food, National food safety standards, 2016, pp. 1-5, National Health and Family Planning Commission of the People's Republic of China.

\* cited by examiner

*Primary Examiner* — Hong T Yoo
(74) *Attorney, Agent, or Firm* — Bayramoglu Law Offices LLC

(57) ABSTRACT

A rapid fermentation method for shrimp paste based on combined strain fortification is provided. *Cladosporium* Z3 and *Enterococcus faecalis* X1 were deposited in the Chinese typical culture preservation center under preservation numbers CCTCC NO: M 2022487 and CCTCC NO: M 2022486, respectively. Two strains were employed to ferment the small hairy shrimp in two steps, utilizing each strain's properties, which enabled the fermentation capacity to be maximized to increase the fermentation speed and stabilize the quality. In addition, the pollution of miscellaneous bacteria is inhibited by strain-enhanced fermentation.

12 Claims, 2 Drawing Sheets

RAPID FERMENTATION METHOD FOR SHRIMP PASTE BASED ON COMBINED STRAIN FORTIFICATION

CROSS REFERENCE TO THE RELATED APPLICATIONS

This application is the national phase entry of International Application No. PCT/CN2022/142877, filed on Dec. 28, 2022, which is based upon and claims priority to Chinese Patent Application No. CN202210571850.1, filed on May 25, 2022, the entire contents of which are incorporated herein by reference.

TECHNICAL FIELD

The present disclosure belongs to the technical field of aquatic products processing, in particular to a rapid fermentation method for shrimp paste based on combined strain fortification.

BACKGROUND

Shrimp paste is a common fermented food in coastal areas of China, Hong Kong and Southeast Asia, which is made by mixing shrimp with salt and grinding it into a sticky state, followed by spontaneous fermentation for a long time. During the fermentation process, the proteins in shrimp paste are decomposed into amino acids under the joint action of microorganisms and various enzymes, giving it unique and delicious flavors. At the same time, a variety of nutrients that are not available before fermentation will be produced, such as various fatty acids, pyrazines, etc. Shrimp sauce is salty and is usually sold as a canned condiment or dried into chunks of shrimp paste for sale. Shrimp paste is popular because of its unique flavor and nutritional properties.

It is challenging to industrialize the production of shrimp paste because the traditional manufacturing process is time-consuming and prone to external factors that result in unstable quality, and the open fermentation method makes it susceptible to contamination by harmful microorganisms that produce harmful substances like biogenic amines and nitrites. Shrimp paste that is naturally fermented requires the addition of a large amount of salt to inhibit the growth of hazardous microorganisms, making it only available in small quantities as a condiment, unsuitable for long-term consumption. Therefore, shrimp paste's ability to be produced and sold is typically severely constrained.

Two main methods of enzyme addition and inoculation are typically used in the quick manufacturing of shrimp paste. By adding proteases, primarily neutral and alkaline proteases, the enzyme addition fermentation method expedites the breakdown of proteins in shrimp pulp into amino acids. Although it has the benefits of decreased salt content and expedited fermentation, the flavor of the finished product falls short of that of commercially available shrimp paste. The inoculation fermentation method is to build a synthetic microbial community by adding biological fermenters, thus inhibiting the growth of other harmful microorganisms and ultimately achieving the purpose of shortening the fermentation time and improving the quality and safety of the product. However, the current single bacteria fermentation or co-fermentation methods make the product flavor improved but still lacking.

The fermentation process of shrimp paste is a slow flora succession process, and these florae assume roles in different fermentation stages. A variety of traditional fermented foods have been explored in stepwise fermentation methods, such as sauerkraut, pork paste, wine, cider, and horseradish sauce, but few studies have investigated the effects of stepwise fermentation of different strains on the flavor formation of shrimp paste.

SUMMARY

To address the shortcomings of the prior art for the fermentation of shrimp paste, the present disclosure provides a rapid fermentation method for shrimp paste based on combined strain fortification. In order to increase the fermentation speed and stabilize the quality, several strains are employed to ferment the small hairy shrimp in two steps, utilizing each strain's properties to the fullest extent possible. In addition, the pollution of miscellaneous bacteria was inhibited by strain-enhanced fermentation, thus the addition of salt was reduced.

Two fermentative strains *Cladosporium* Z3 and *Enterococcus faecalis* X1 used in the present disclosure were screened in shrimp paste samples produced by Zhongxin aquatic products Co., Ltd, Cangzhou City, Hebei Province. The samples were produced in July 2020 and the strains were screened at Jiangsu University, Zhenjiang, Jiangsu Province, China in July 2020. *Cladosporium* Z3 had strong protease and lipase production ability, while *Enterococcus faecalis* X1 had a strong ability to produce protease and acid, which could inhibit the growth and reproduction of *Cladosporium* Z3. *Cladosporium* Z3 and *Enterococcus faecalis* X1 had been stored in the Chinese typical culture preservation center under preservation numbers CCTCC NO: M 2022487 and CCTCC NO: M 2022486, respectively.

The technical solution of the present disclosure is a rapid fermentation method for shrimp paste based on combined strain fortification, and comprising the following steps.

(1) Cutting hairy shrimps into a shrimp slurry, adding an edible salt at a predetermined ratio in the shrimp slurry, and mixing the resulting shrimp slurry well to obtain a shrimp pulp.

(2) Inoculating *Cladosporium* Z3 in a YPD liquid medium for activation, and then applying the culture solution to a YPD solid medium for secondary incubation; subsequently, adding sterile saline to a plate and scraping the mycelium from the surface of the medium; then shaking and filtering the solution to remove the mycelium, and diluting the filtrate with sterile saline to obtain a spore suspension of *Cladosporium* Z3, which is stored under a preservation number CCTCC NO: M 2022487.

(3) Inoculating *Enterococcus faecalis* X1 in a YPD liquid medium for activation and a seed solution was obtained after cultivation. Subsequently, centrifuging the seed solution to obtain a bacterial sludge and resuspending the bacterial sludge in sterile saline to obtain a bacterial suspension of *Enterococcus faecalis* X1 with a preservation number CCTCC NO: M 2022486.

(4) Inoculating the spore suspension of *Cladosporium* Z3 prepared in step (2) into the shrimp pulp prepared in step (1) for one-step fermentation to obtain a fermentation primary product.

(5) Inoculating the *Enterococcus faecalis* X1 bacterial suspension prepared in step (3) into the fermentation primary product made in step (4) for two-step fermentation and obtained a rapidly fermented shrimp paste product.

The preferred variables for the aforementioned technique are as follows:

The salt added in step (1) is 5% to 10% of the shrimp pulp mass.

The time of *Cladosporium* Z3 activation culture in step (2) is 2-4 days, the temperature is 20-30° C., and the speed is 100-170 rpm. The time of secondary culture of YPD solid medium is 2-6 days, and the temperature is 20-30° C.

The amount of sterile saline in the plate in step (2) should be sufficient to cover the colonies on the surface of the medium (3-8 mL), and the concentration of *Cladosporium* Z3 spore suspension is $1\times10^6$-$1\times10^7$ CFU/mL.

The formulation of the YPD liquid medium (1 L) described in steps (2) and (3) is: yeast paste 10 g/L, tryptone 10 g/L, glucose 10 g/L, sterilized at 121° C. for 20 min.

The formulation of the YPD liquid medium (1 L) described in steps (2) and (3) is: yeast paste 10 g/L, tryptone 10 g/L, glucose 10 g/L, agar powder 10 g/L, sterilized at 121° C. for 20 min.

The time of *Enterococcus faecalis* X1 described in step (3) activation culture is 24-48 h, the temperature is 20-30° C., and the speed is 100-170 rpm. The concentration of bacterial suspension is $1\times10^7$-$1\times10^8$ CFU/mL.

The conditions of centrifugation described in step (3) are 4° C., 6000-8000 rpm, and 10-15 min.

The process parameters of the one-step fermentation in step (4) are as follows: the fermentation temperature is 20-25° C., the fermentation time is 10-20 days, and the dosage ratio of the *Cladosporium* Z3 spore suspension to the shrimp pulp is 1-6 mL: 100 g.

The process parameters of the two-step fermentation in step (5) are as follows: the fermentation temperature is 20-30° C., the fermentation time is 2-15 days, and the dosage ratio of the *Enterococcus faecalis* X1 seed liquid to the initial fermentation product is 1-6 mL: 100 g.

Beneficial effects of the present disclosure are as follows: the rapid fermentation method for shrimp paste based on combined strain fortification has the advantage of high efficiency, which can significantly shorten production time, improve efficiency, and lower the cost. This method inoculates specific functional strains of bacteria to become the dominant strain in the shrimp paste fermentation environment, further inhibiting the growth of harmful strains of bacteria, and achieving the purpose of improving the stability and safety of shrimp paste products. The shrimp paste produced by this method has a low salt content, which is more in line with the requirements of food health. The two-step rapid fermentation method of shrimp paste with strain enhancement achieves rapid and stable fermentation of shrimp paste and provides theoretical and technical support for the industrial production of shrimp paste.

The two-step rapid fermentation method of shrimp paste based on strain augmentation yields shrimp paste with a low salt level, which is more in accordance with food healthy requirements. It can produce shrimp paste quickly and consistently, offering theoretical and technical support for the industrial production of shrimp paste.

DETAILED DESCRIPTION OF THE EMBODIMENTS

Figure 1:
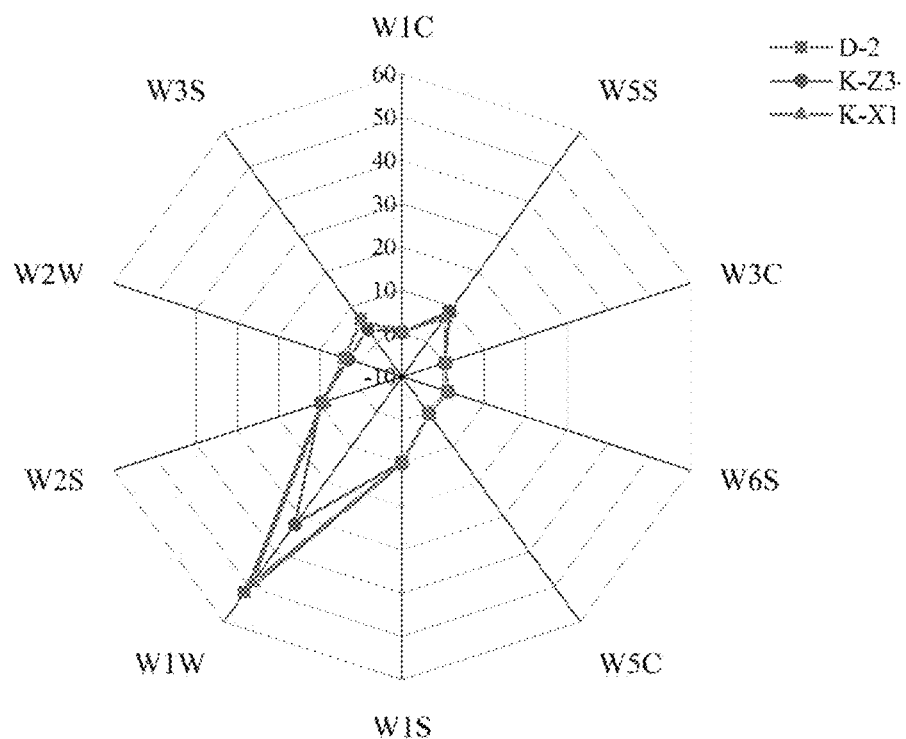
FIG. 1 Radar plot of volatile components in the three groups of fermented shrimp paste samples.

The current invention will be discussed in greater detail below about the embodiments to comprehend it better. However, the present invention is not limited to the following embodiments, so the embodiments do not limit the present disclosure in any way.

The two fermentative strains *Cladosporium* Z3 and *Enterococcus faecalis* X1 used in the present disclosure were screened in shrimp paste samples produced by Zhongxin aquatic products Co., Ltd, Cangzhou City, Hebei Province. The samples were produced in July 2020 and the strains were screened at Jiangsu University, Zhenjiang, Jiangsu Province, China in July 2020. *Cladosporium* Z3 had strong protease and lipase production ability, while *Enterococcus faecalis* X1 had a strong ability to produce protease and acid, which could inhibit the growth and reproduction of *Cladosporium* Z3. *Cladosporium* Z3 and *Enterococcus faecalis* X1 had been stored in the Chinese typical culture preservation center under preservation numbers CCTCC NO: M 2022487 and CCTCC NO: M 2022486, respectively, both are preserved until Apr. 25, 2022.

Amino acid nitrogen (AAN) content in the samples was determined by formaldehyde titration, referring to GB5009.235-2016. According to GB/T5009.228-2016, the total volatile basic nitrogen (TVB-N) content in the samples was determined by the microdiffusion method. Moreover, pH was determined by SevenExcellence S400-Basic after the sample was diluted 10 times. Electronic nose (E-nose) was used to detect the overall flavor profile of shrimp paste products, and Solid-phase microextraction gas chromatography-mass spectrometry (SPME-GC-MS) was used to detect specific volatile components Sensory assessment analysis of fast-fermented shrimp paste samples was performed using quantitative descriptive analysis. The shrimp paste flavor sensory evaluation panel consisted of 15 volunteers (eight women and seven men, aged 22-45 years) who were professionally trained in flavor evaluation. Scores ranged from 0 to 9, and the flavors of the fast-fermented shrimp paste samples were divided into eight main components: shrimp flavor, freshness, saltiness, sweetness, fermented flavor, fishy flavor, ammonia flavor, and bitterness, and finally, the overall favorite of the shrimp paste was used as the final score.

The shrimp paste products produced using the present invention's method were contrasted with those produced using fermentation without starters and with *Cladosporium* Z3, and the differences between the various shrimp paste products were assessed using the same test procedure.

Comparative Example 1: fermentation without the addition of fermenter strains (Group D).

The shrimp pulp was obtained by pulverizing the small hairy shrimp, adding 6% of the shrimp pulp mass with salt, and stirring well. Subsequently, the samples were placed in a constant temperature incubator with the speed at 100 rpm and fermented at 21° C. for 12 days, followed by 25° C. for 4 days.

Comparative Example 2: fermentation with the addition of *Cladosporium* Z3 (Group K-Z3).

The shrimp pulp was obtained by pulverizing the hairy shrimp, adding 6% salt to the mass of shrimp pulp, and mixing well. *Cladosporium* Z3 spore suspension at a concentration of 2*10$^6$ CFU/mL was then inoculated into the shrimp pulp in a ratio of 4 mL: 100 g (V/W). The fermentation was carried out in a constant-temperature incubator at 21° C. for 12 d at a speed of 100 rpm.

Example 1: Two-Step Rapid Fermentation Based on Strain Fortification (Group K-X1)

The seed solution of *Enterococcus faecalis* X1 was inoculated into the samples of group K-Z3 in a ratio of 4 mL: 100 g (V/W) with the fermentation primary product. The fermentation was then carried out at 25° C. for 4 d at a speed of 100 rpm.

Figure 2:
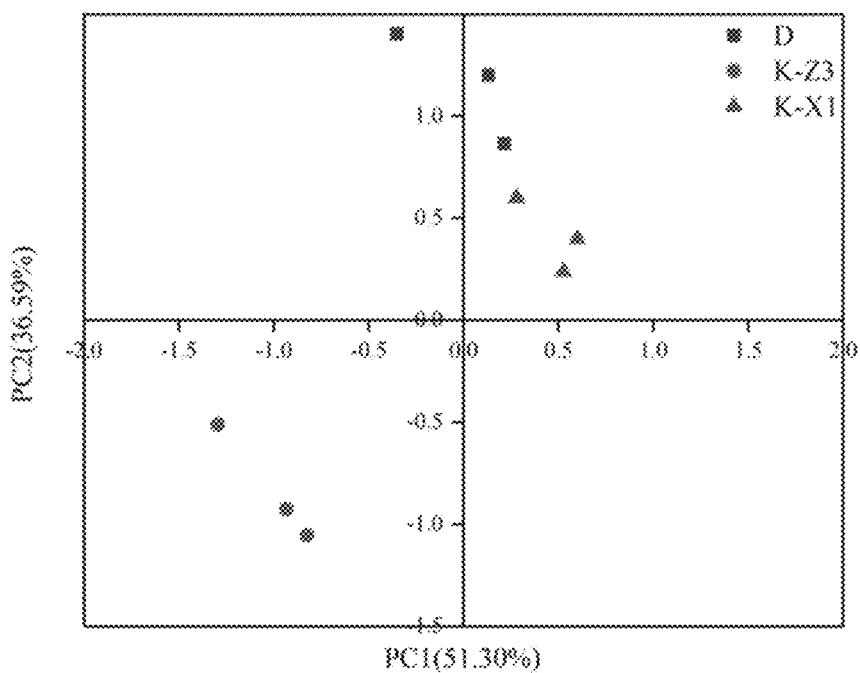
FIG. 2 Principal component analysis (PCA) of volatile components in the three groups of fermented shrimp paste samples.
Figure 3:
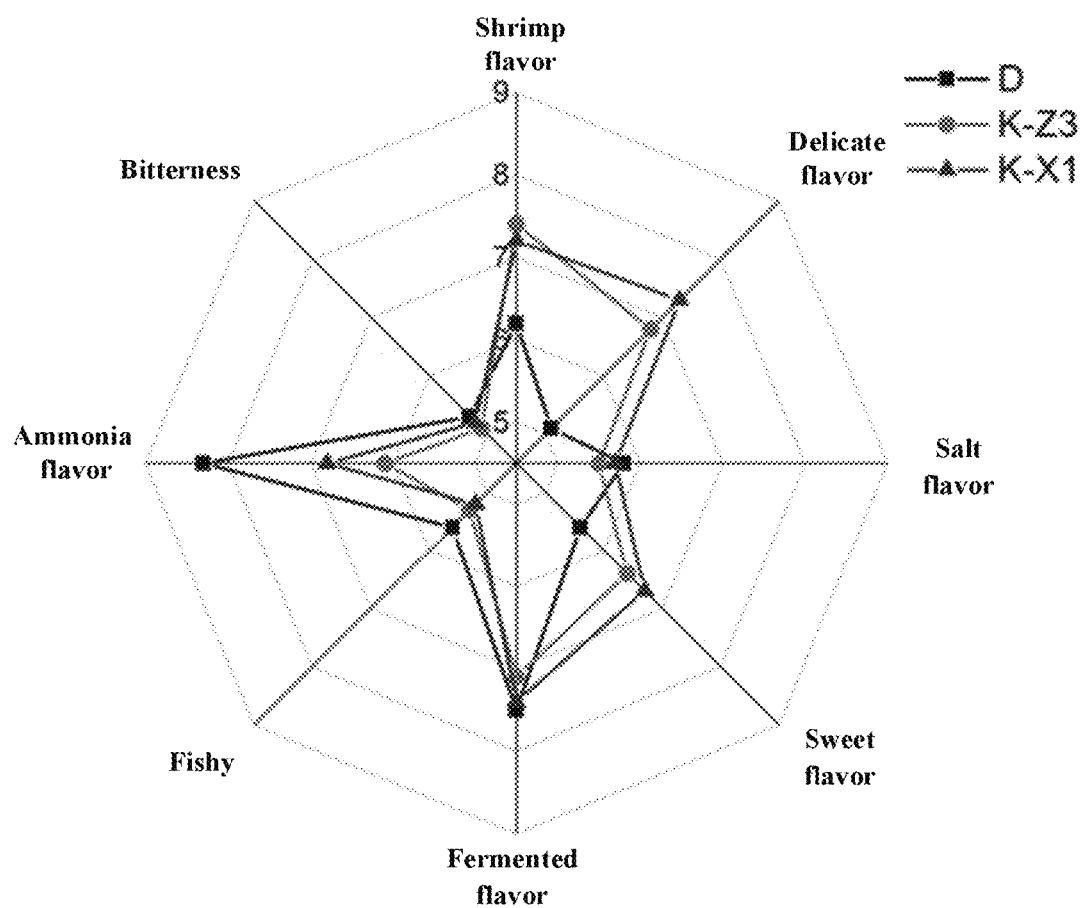
FIG. 3 Radar diagram of sensory scores of the three fermented shrimp paste sample groups.

The same physical and chemical parameters testing methods and sensory evaluation methods were used to compare the differences between the three groups of products, and the specific results are shown in Tables 1-2 and FIGS. 1-3.

Specifically, as shown in Table 1, the pH of the fermented shrimp paste was alkaline, *Cladosporium* Z3 was able to produce alkaline substances, and the inoculation of *E. faecalis* X1 slowed down the increase of pH to some extent. The AAN content of the fermented shrimp paste inoculated with starters was higher than that of the non-inoculated control group, indicating that fermentation with starters effectively increased the AAN content in the fermented shrimp paste. This improved the fermentation degree and allowed for more adequate hydrolysis of the proteins in the shrimp paste. TVB-N is the key indicator of the spoilage degree of shrimp paste, and its higher content denotes a greater degree of deterioration of the fermented product. The fact that the TVB-N significantly decreased after being inoculated with starters suggested that the strains in the starter may eventually dominate the flora, preventing the growth of spoiling bacteria. As a result, two-step fermentation can improve shrimp paste fermentation rate and product quality as a speedy shrimp paste fermentation method.

TABLE 1

Results of pH, AAN, and TVB-N

| Sample Name | pH | AAN (g/100 mL) | TVB-N (mg/100 mL) |
|---|---|---|---|
| D | 7.98 | 1.33 | 332.5 |
| K-Z3 | 8.09 | 1.41 | 228.5 |
| K-X1 | 8.12 | 1.44 | 239.5 |

The E-nose was used to examine the overall flavor profile of the three groups of samples, and the results were shown in FIG. 1. The radar plot results showed that there was a significant difference in sulfide content (W1W) among the three groups of samples, and the sulfide content in the samples from the comparative example 2 group was higher than those from the example 1 and comparative example 1 groups. Additionally, the comparative example 2 group samples had fewer long-chain alkanes than those from the example 1 group and comparative example 1 group.

FIG. 2 shows principal component analysis (PCA) of volatile components in the three groups of fermented shrimp paste samples. The results show that the variance contribution of PC1 and PC2 was 51.30% and 36.59%, and the cumulative total contribution of the two principal components reached 87.89%, which can effectively reflect most of the information of the original data. All three groups of samples were relatively independent, indicating that there were some differences in the types and contents of volatiles. Especially, the samples in groups comparative example 2 and example 1 were significantly different from those in comparative example 1 group, indicating that the enhanced starters had a greater influence on the production of volatiles in the samples.

A total of 65 volatile compounds were detected by GC-MS in the three sets of fermented shrimp paste samples (Table 3), including 18 alcohols, 8 ketones, 7 esters, 2 acids, 10 hydrocarbons, 3 amines, 4 pyrazines, 2 aldehydes, and 10 other compounds. The types and contents of volatile compounds were increased in the samples of example 1. Esters usually smelled fruity and flowery and influenced the overall flavor formation of shrimp paste. The type and content of esters in the shrimp paste sample in example 1 increased, indicating that the fermentation method of the present disclosure was able to promote the production of esters. Both aldehydes and pyrazines contributed significantly to the formation of flavor in shrimp paste. Aldehydes were not detected in the samples of comparative example 1, presumably due to the short fermentation time and the absence of inoculation with functional strains, which hindered the formation of aldehydes in the short term. In contrast, two aldehydes were detected in the samples of comparative example 2 and example 1, suggesting that inoculation with starters accelerated the formation of flavor substances to some extent. The contents of 2,5-dimethylpyrazine, 2,3,5-trimethylpyrazine and 3-ethyl-2,5-methylpyrazine in the shrimp paste samples of example 1 were higher than those of comparative examples 1 and 2. Trimethylamine is the primary amine molecule in aquatic products and typically has a fishy taste. However, its content in the shrimp paste samples in example 1 decreased. All the results suggested that the method of the present disclosure could improve the flavor of the rapidly fermented shrimp paste products.

TABLE 2

Volatile compounds in three groups of fermented shrimp paste samples detected by GC-MS

| Compounds | Relative amount (%) | | |
|---|---|---|---|
| | D | K-Z3 | K-X1 |
| Alcohols | | | |
| 1-Butanol, 3-methyl- | 37.77 | 29.25 | 16.39 |
| Phenylethyl Alcohol | 7.86 | 6.95 | 9.15 |
| 1-Penten-3-ol | 0.08 | 0.09 | ND |
| 1-Pentanol | 0.73 | 0.53 | ND |
| 1-Pentanol, 2-ethyl-4-methyl- | 0.61 | ND | ND |
| 1-Propanol, 3-(methylthio)- | 0.83 | ND | ND |
| Benzenemethanol, 3-hydroxy-5-methoxy- | 0.32 | ND | ND |
| 1-Butanol, 2,3-dimethyl- | 0.04 | ND | ND |
| Ethanol | ND | 7.22 | ND |
| 1-Propanol | ND | 0.20 | ND |
| 1-Octanol, 2,2-dimethyl- | ND | 0.16 | ND |
| 1-Propanol, 2-methyl- | ND | 0.70 | ND |
| 2-Nonen-1-ol | ND | 0.40 | ND |
| 1-Hexanol, 2-ethyl- | ND | 0.20 | ND |
| 2-Propyl-tetrahydropyran-3-ol | ND | ND | 2.18 |
| 4,5-Octanediol, 2,7-dimethyl- | ND | ND | 0.96 |
| 2-Heptanol, 5-ethyl- | ND | ND | 0.09 |
| 1-Octyn-3-ol, 4-ethyl- | ND | ND | 0.35 |
| Ketones | | | |
| Acetone | 1.48 | 0.72 | 1.89 |
| 2-Butanone | 0.92 | 0.53 | 2.67 |
| 2-Nonanone | 0.66 | 0.09 | 0.38 |
| Cyclohexanone, 4-ethyl- | 0.46 | 0.10 | 0.18 |
| 3-Hexanone | 0.09 | ND | 0.05 |
| 2-Heptanone | 0.55 | ND | 0.51 |
| 3-Heptanone, 5-methyl- | 0.56 | 0.25 | ND |
| Benzyl isobutyl ketone | 0.64 | ND | ND |
| Esters | | | |
| Butanoic acid, 2-methyl-, 3-methyl butyl ester | 0.14 | ND | ND |
| Hexanoic acid, 2-phenylethyl ester | ND | 0.23 | ND |

TABLE 2-continued

Volatile compounds in three groups of fermented shrimp paste samples detected by GC-MS

| | Relative amount (%) | | |
|---|---|---|---|
| Compounds | D | K-Z3 | K-X1 |
| Tert-butyl N-benzylcarbamate | ND | ND | 0.64 |
| Pentanoic acid, pentyl ester | ND | ND | 0.08 |
| Octadecanoic acid, ethenyl ester | ND | ND | 0.70 |
| 7-Methyl-Z-tetradecen-1-ol acetate | ND | ND | 9.08 |
| N,N'-Bis(Carbobenzyloxy)-lysine methyl(ester) | ND | ND | 2.71 |
| Acids | | | |
| 1,2,4-Benzenetricarboxylic acid | 0.28 | 0.82 | 0.86 |
| Acetic acid, hydroxy- | ND | 0.33 | ND |
| Hydrocarbons | | | |
| Undecane, 5,7-dimethyl- | 0.08 | ND | 0.12 |
| Heptane, 2,4-dimethyl- | 0.05 | ND | 0.10 |
| Octane | 0.11 | ND | ND |
| Decane, 2,4-dimethyl- | 0.08 | 0.12 | ND |
| Octane, 5-ethyl-2-methyl- | ND | 0.05 | ND |
| Heptane, 2,3-epoxy- | ND | 0.09 | ND |
| Octane, 4-methyl- | ND | 0.03 | ND |
| Octane, 2,4,6-trimethyl- | ND | 0.02 | ND |
| 1-Hexene, 3,5,5-trimethyl- | 1.29 | 0.75 | ND |
| 1,3,5-Cycloheptatriene | ND | 0.08 | ND |
| Amines | | | |
| Methylamine, N,N-dimethyl- | 21.47 | 18.33 | 19.59 |
| Ethanamine, N-methyl- | ND | 1.06 | ND |
| Acetamide, N-methyl-N-[4-(3-hydroxy pyrrolidinyl)-2-butynyl]- | ND | ND | 6.01 |
| Pyrazines | | | |
| Pyrazine, 2,5-dimethyl- | 1.77 | 2.12 | 2.89 |
| Pyrazine, trimethyl- | 0.19 | 0.27 | 0.56 |
| Pyrazine, 2-ethyl-3,5-dimethyl- | 1.96 | 0.01 | ND |
| Pyrazine, 3-ethyl-2,5-dimethyl- | ND | 2.81 | 4.00 |
| Aldehydes | | | |
| Butanal, 3-methyl- | ND | 0.09 | 0.05 |
| Benzaldehyde | ND | 0.22 | 0.12 |
| others | | | |
| Oxime-, methoxy-phenyl-_ | 1.07 | 0.85 | ND |
| Pyrimidine, 4-methyl- | 0.04 | ND | 0.11 |
| Indole | 17.62 | 22.77 | 16.45 |
| Hydrazinecarboxamide | 0.02 | ND | ND |
| Pyridine, 2-methoxy-5-nitro- | ND | 0.35 | ND |
| Propanoic acid, 3-hydroxy-, hydrazide | 0.06 | ND | ND |
| 4-Hydroxybutyric acid hydrazide | 0.03 | 0.06 | ND |
| Hydrazine, 2-butenyl- | 0.12 | 0.01 | 0.01 |
| Acetic acid, hydrazide | ND | 0.03 | 0.15 |
| Butyric acid hydrazide | ND | 0.08 | ND |

The result of the sensory evaluation of the three groups of samples is shown in FIG. 3, which signified that there were some differences between the samples of different groups. Among them, the overall flavor of comparative example 1 was dominated by ammonia and fermentation flavor, which was consistent with the results of higher TVB-N content in samples of comparative example 1. It may be due to the lower salt content in the raw material of shrimp paste in comparative example 1 and the absence of the fermentation agent, which led to the proliferation of spoilage microorganisms during the fermentation process. The excessive fermentation and the production of large amounts of biogenic amines and other substances accelerated the spoilage of shrimp paste samples. The shrimp flavor, freshness, sweetness, and fermentation flavor predominated in the samples from the comparative example 2 and example 1, which is coherent with the higher AAN content and lower TVB-N content in these two groups of samples. It was speculated that this is most probably because of the inoculated fermentative agent's ability to emerge as the dominant colony quickly, which inhibited the growth of spoilage microbes in the shrimp raw material and prevented over-fermentation, spoiling, and excessive biogenic amine synthesis. The fortification of starters promoted the hydrolysis of proteins and fatty acids in the raw materials, which in turn produced more flavor substances and imparted more freshness and flavor to the shrimp paste. In comparison to samples in comparative example 2, samples in example 1 scored more favorably for freshness and sweetness and had a softer overall flavor. All results evidenced that the two-step fermentation method using enhanced starters could reduce the salt content, shorten the fermentation time and improve the quality of shrimp paste products.

Note: The above examples are used only to illustrate the present disclosure and not to limit the technical solutions described herein. Therefore, although the present disclosure has been described in detail in this specification concerning the above examples. It should be understood by ordinary technicians in the art that modifications or equivalent substitutions can still be made to the present disclosure, and all technical solutions and improvements thereof that do not depart from the spirit and scope of the present disclosure should be covered within the scope of the present claims.

What is claimed is:

1. A rapid fermentation method for shrimp paste based on combined strain fortification, comprising the following steps:
   (1) cutting hairy shrimps into a shrimp slurry, adding an edible salt at a predetermined ratio to the shrimp slurry, and mixing a resulting shrimp slurry well to obtain a shrimp pulp, wherein the edible salt is added in an amount of 5% to 10% by mass of the shrimp pulp;
   (2) inoculating *Cladosporium* Z3 in a yeast extract peptone dextrose (YPD) liquid medium for activation, and then applying a culture solution to a YPD solid medium for secondary incubation; subsequently, adding sterile saline to a plate and scraping a mycelium from a surface of the medium; then shaking and filtering a resulting solution to remove the mycelium, and diluting a filtrate with sterile saline to obtain a *Cladosporium* Z3 spore suspension, which is stored under a preservation number CCTCC NO: M 2022487;
   (3) inoculating *Enterococcus faecalis* X1 in a YPD liquid medium for activation and a seed solution is obtained after cultivation; subsequently, centrifuging the seed solution to obtain a bacterial sludge and resuspending the bacterial sludge in sterile saline to obtain an *Enterococcus faecalis* X1 spore suspension with a preservation number CCTCC NO: M 2022486;
   (4) inoculating the *Cladosporium* Z3 spore suspension prepared in the step (2) into the shrimp pulp prepared in the step (1) for one-step fermentation to obtain a fermentation primary product, wherein a dosage ratio of the *Cladosporium* Z3 spore suspension to the shrimp pulp is 1-6 mL: 100 g, a fermentation temperature is 20-25° C., and a fermentation time is 10-20 days; and
   (5) inoculating the *Enterococcus faecalis* X1 spore suspension prepared in the step (3) into a fermentation primary product prepared in the step (4) for two-step fermentation to obtain a rapidly fermented shrimp paste product, wherein a dosage ratio of the *Enterococcus faecalis* X1 spore suspension to the fermentation primary product is 1-6 mL:100 g, a fermentation temperature is 20-30° C., and a fermentation time is 2-15 days.

2. The rapid fermentation method for shrimp paste based on combined strain fortification according to claim 1 wherein, a time of the activation the *Cladosporium* Z3 in the step (2) is 2-4 days, a temperature is 20-30° C., and a speed is 100-170 rpm; a time of the secondary incubation of the YPD solid medium is 2-6 days, and a temperature is 20-30° C.

3. The rapid fermentation method for shrimp paste based on combined strain fortification according to claim 1 wherein, an amount of the sterile saline in the plate in the step (2) is sufficient to cover colonies on the surface of the medium, and a concentration of the *Cladosporium* Z3 spore suspension is $1\times10^6-1\times10^7$ CFU/mL.

4. The rapid fermentation method for shrimp paste based on combined strain fortification according to claim 1 wherein, the YPD liquid medium in the step (2) or the step (3) has a formulation per 1 L of: yeast paste 10 g/L, tryptone 10 g/L, and glucose 10 g/L, and the YPD liquid medium is sterilized at 121° C. for 20 min.

5. The rapid fermentation method for shrimp paste based on combined strain fortification according to claim 1 wherein, the YPD solid medium (1 L) in the steps (2) has a formulation per 1 L of: yeast paste 10 g/L, tryptone 10 g/L, glucose 10 g/L, agar powder 10 g/L, and the YPD solid medium is sterilized at 121° C. for 20 min.

6. The rapid fermentation method for shrimp paste based on combined strain fortification according to claim 1 wherein, a time of the activation of the *Enterococcus faecalis* X1 in the step (3) is 24-48 h, a temperature is 20-30° C., and a speed is 100-170 rpm; a concentration of the *Enterococcus faecalis* X1 spore suspension is $1\times10^7-1\times10^8$ CFU/mL; and the centrifugation is conducted at 4° C. and 6000-8000 rpm for 10-15 min.

7. A shrimp paste prepared by the method according to claim 1.

8. A shrimp paste prepared by the method according to claim 2.

9. A shrimp paste prepared by the method according to claim 3.

10. A shrimp paste prepared by the method according to claim 4.

11. A shrimp paste prepared by the method according to claim 5.

12. A shrimp paste prepared by the method according to claim 6.

* * * * *